United States Patent [19]

Klemm et al.

[11] 4,273,143
[45] Jun. 16, 1981

[54] PERMANENT WAVE COMPOSITION

[75] Inventors: Ernest J. Klemm, Thornwood, N.Y.; Walter W. Edman, Westport; Frances E. Erskine, Fairfield; Everett G. McDonough, Stamford, all of Conn.

[73] Assignee: Zotos International, Inc., Darien, Conn.

[21] Appl. No.: 58,264

[22] Filed: Jul. 17, 1979

[51] Int. Cl.³ ............................................. A45D 7/00
[52] U.S. Cl. ......................................... 132/7; 424/71
[58] Field of Search .................... 132/7, 9; 424/71, 72

[56] References Cited

U.S. PATENT DOCUMENTS

| | | | |
|---|---|---|---|
| 2,719,815 | 10/1955 | Sanders | 424/72 |
| 2,738,304 | 3/1956 | Arnold | 424/72 |
| 3,193,463 | 7/1965 | Schweizer | 424/72 |

Primary Examiner—G. E. McNeill
Attorney, Agent, or Firm—Mattern, Ware, Davis & Stoltz

[57] ABSTRACT

By providing a single wrapping composition capable of wetting and conditioning unbleached hair fibers while simultaneously protecting, equalizing and conditioning bleached hair fiber so that both the bleached and unbleached hair fibers are capable of responsive interaction with a waving or processing lotion, a unique permanent waving system is achieved which allows a head of hair having both bleached and unbleached hair fiber inseparably mixed, to be permanently waved in a single, uniform application and treatment. In order to assure that the bleached hair fibers will be capable of reacting with the waving or processing lotion, the wrapping composition should comprise an aqueous solution incorporating a hair substantive compound containing a lipoidal alkyl chain having ten or more carbon atoms and a disulfide derivative of a mercaptan with a substituent group. Preferably, the respective chemical compounds are those containing a quaternary ammonium group and a dithio derivation of a thioglycolate. In the preferred embodiment, a special processing composition, specifically formulated for reactive interaction with the wrapping composition, is employed.

18 Claims, No Drawings

PERMANENT WAVE COMPOSITION

TECHNICAL FIELD

This invention relates to the art of permanently altering the shape of human hair, especially to improvements in the method of permanently waving hair, and novel compositions of matter by which such an improvement may be attained.

This invention is more specifically directed at the permanent waving of an area of hair on a human head where some of the individual hair fibers in the area have been damaged while other individual hair fibers remain in a relatively undamaged state, and the two different types are incapable of being easily separated.

BACKGROUND ART

Generally damaged hair fibers and relatively undamaged hair fibers coexist on almost every head. Since the hair grows outward from the scalp it is constantly being subjected to mechanical damage, particularly from combing and brushing, and the detrimental action of sunlight, especially after contact with water containing chlorine. Also shampooing, permanent waving, coloring and especially treatments involving the use of hydrogen peroxide, all have an accumulative effect that causes hair older than one year (6 inches long) to have distal ends on each hair fiber that are more damaged than the proximal ends near the scalp.

Although the permanent waving of such hair can be done with conventional compositions, the areas of the damaged hair fibers must be segregated from the undamaged hair fibers and treated differently. This segregation is necessary for various well-known reasons. First, damaged hair, in general, and bleached chemically or colored hair, in particular, is much more susceptible to being broken by excessive handling. In addition, depending upon which of the seven independent, distinct and recognized stages of bleaching the hair fibers have attained, the chemical reactivity of these hair fibers will be significantly different from the reactivity of undamaged hair as well as from the reactivity of a bleach hair fiber at a different bleaching stage.

In certain types of bleached heads of hair, segregation of the different hair fibers is not possible. Prior to our invention, such heads of hair have never been able to be permanently waved.

For example, in the frosting of hair a cap is placed over the hair area of the scalp. This cap may have 300 or 400 small openings. Small bundles of hair fibers are pulled through these holes, the amounts of the hair and the location and number of the holes selected will depend on the pattern of frosting desired. The number of the individual hair fibers through each hole may vary from 50 to 250.

It is rare for more than half of the holes to be used, but it is possible to have as high as 50% of the hair bleached. These hair fibers, however, may be bleached to the highest of the recognized seven stages of bleaching. The highly bleached hair thus can represent up to 50% of the entire head and it would be exceedingly difficult, if not impossible, to segregate these sections in order to give them a different treatment, a different composition and/or a different method, in order to obtain a permanent wave without breakage.

It is the principal object of this invention to provide a permanent hair waving system wherein a head of hair having up to 50% bleached hair fibers can be permanently waved without requiring the hair to be segregated into groups of hair fibers of similar condition.

Another object of this invention is to provide a permanent hair waving system having the characteristic features defined above wherein the system is easy to use and easy to employ without requiring special training.

Another object of this invention is to provide a permanent hair waving system having the characteristic features defined above wherein frosted or tipped heads of hair can be permanently waved as easily and conveniently as unbleached heads of hair.

A further object of this invention is to provide a permanent hair waving system having the characteristic features defined above wherein heads of hair having unsegregatable mixed hair fibers of unbleached and varying stages of bleached hair fibers can be permanently waved as easily and conveniently as a head of hair having hair fibers of substantially uniform condition throughout.

Other and more specific objects will in part be obvious and will in part appear hereinafter.

DISCLOSURE OF INVENTION

With our invention, these prior art limitations and problems are eliminated. Now, for the first time, we are able to effectively and safely, without breakage of the bleached hair, permanently wave heads of hair without requiring the segregation of bleach hair fibers. Using our invention, all of the hair on the entire head is treated in the same manner, using the same compositions.

Another advantage of our invention is that the conventional method of permanently waving human hair on the head is employed without deviation. In this way, our novel system is easily employed, without requiring special steps to be learned.

The conventional method for permanently waving human hair, which is employed using our invention, is to first shampoo the entire head of hair and then towel dry. After towel drying, the hair is wetted and wound on rollers. With our invention, this procedure is followed, except that our special wetting or "wrapping" composition lotion is employed. After the hair is wound, the wound tresses on the rods are then treated with a waving lotion. With our invention, our special waving or "processing" composition lotion is employed at this stage. The next conventional step is for the hair to be permitted a processing time, which can be shortened by external heat applications, with or without a covering. Alternatively, the waving or "processing" lotion can be preheated by a chemical reaction or an external heat source.

After the processing, the hair is rinsed with water and, as a final step, conventional neutralizing with a lotion containing an oxidizer, such as hydrogen peroxide or a soluble bromate, is applied in usually two steps, while the hair is on the rod and after it is removed from the rod. Finally, the hair is rinsed with water.

Our unique composition for the wetting or "wrapping" lotion, which is used to wet the hair prior to winding the hair on the rod, comprises an aqueous solution or emulsion of ingredients selected to perform certain functions. This "wrapping" lotion combines these functional properties so that the "wrapping" lotion acts as an equalizer, a conditioner, and a protector.

In order to best understand the operation of our unique wrapping composition, it is important to remember that the moisture content of dry hair is directly dependent on the content of the moisture in the ambient air, namely the relative humidity of air. In general, the percentages by weight of moisture in bleached hair and unbleached hair in the same ambient air are very close. However, when they are placed in water, the bleached hair will absorb a greater amount of water; the more bleached the hair the greater the absorption of water. For example, as the bleaching stage approaches the 7th stage, the bleached hair will approach an amount of water in the bleached hair that is twice as great as the amount of water in unbleached hair.

Using this principal, our aqueous wrapping lotion delivers its ingredients inside the bleached hair, with the amounts delivered being greater the more bleached the hair. In addition, the ingredients of the "wrapping" composition have a far easier entry into the porous bleached hair fiber.

As would be apparent to one skilled in the art, the amount of the water employed in the "wrapping" composition plays a role by giving a greater dilution of the subsequently applied waving or "processing" lotion. Consequently, the concentration of the active ingredients of the "processing" lotion inside the hair fibers of the bleached hair could be substantially less than that of the unbleached hair. Furthermore, the greater the bleaching of the hair, the more the concentration would be reduced by the water present.

In order to avoid this undesirable dilution effect from occurring, the ingredients of the "wrapping" composition are specifically selected to play important roles in conditioning and/or protecting the bleached hair fiber without interfering with the waving action of subsequently applied "processing" composition.

In order to best understand the operation of compositions, it is important to remember that in normal (unbleached) hair the three major bonds that hold the configuration of the hair and are responsible for the strength of the hair are: salt linkages, disulfide bonds, hydrogen bonds.

SALT LINKAGES

Hair is a protein produced from units known as "amino acids". A high proportion of these are diamino and dicarboxylic "amino acids" and thus the hair fiber is amphoteric in character. Since the number of free acid and basic groups are approximately equal, the hair's mechanical properties (e.g., strength) is at its maximum at neutrality (pH 7). For example, the fiber becomes easier to stretch as the pH increases or decreases from pH 7. The cohesion of hair is also demonstrated by the minimum swelling in water at neutrality.

DISULFIDE BONDS

Hair is a unique protein, known as "keratin," because it contains a very significant amount of an amino-acid (cystine) that contains the element sulfur, in addition to the elements nitrogen, oxygen, carbon and hydrogen. In the natural synthesis of hair the element sulfur covalently links adjacent polypeptide chains (K) through two sulfur atoms (S—S) to give keratin protein (K—S—S—K). Only by chemical action can this covalent linkage be broken.

HYDROGEN BONDS

Because they are so numerous, the hydrogen bonds, involving the amino hydrogen and the carbonyl oxygen of the amide linkages, are most important. Water, particularly in the monomolecular state as occurs with moisture in the air (humidity), can weaken these bonds, by becoming a part of a hydrogen bonding structure. Thus some hydrogen bond strength will remain even when the hair is wet with water. More powerful hydrogen bond breakers, like high concentration of lithium bromide and urea are required for complete breakage of all hydrogen bonds.

As long as the hair fiber is dry, the strength of the hair fiber is not reduced. For example, a straight hair wet with water and held by mechanical force in a curly configuration while it dries will remain in a curly shape due to the formed hydrogen bonds and salt linkages and it will not return to its straight shape so long as it remains dry. However, unless mechanically restrained, upon being wet with water the hair will lose its curly configuration and become straight. This is due to the fact that in water the dominant bond is the "disulfide" bond. In the dry state, the dominant bonds are the salt linkages and the hydrogen bonds.

The disulfide bond can be broken and when this is done the wet hair is weakened. The loss in strength, as measured by the force to stretch the hair, is directly related to the number of disulfide bonds broken.

These disulfide bonds may be broken by reduction, generally represented by KSSK→2KSH, or by oxidation, generally represented by KSSK→2KSO$_3$H. The breaking by reduction may be reversed and this is the basis of permanent waving with "thioglycolate" (mercaptans). The breaking by oxidation is not reversible, and this is the reaction that occurs in bleaching which, as the color is destroyed, changes the physical and chemical properties of the hair. The smaller the number of KSSK that remain after bleaching the more difficult it becomes to permanently wave the hair. On the other hand, it becomes easier, less mechanical force is required, to retain a naturally straight hair in a curly configuration.

The formation of the KSO$_3$H creates a new acidic group that is a stronger ionizing group than the natural carboxylic acid group. Thus the greater wet strength due to salt linkages will not be at pH 7 but at some lower figure. Generally, the greater the bleaching the lower the pH, with tipping and frosting having a pH range between about 4 and 5.

Even in this pH range, the hydration of the additional sulphonic acid group will result in greater swelling of the bleached hair than unbleached hair at pH 7. The greater the swelling of the hair fiber the more vertical become the distal edges of the overlapping cuticle scales. Also, tipping and frosting are done on older sections of the hair fiber where the cuticle has already been subjected to abuse by more repeated combings. It is thus important that these differences in the surfaces, as well as the differences in the three major bonds of a bleached hair fiber and a normal hair fiber be recognized if a satisfactory permanent wave is to be imparted to a tress that contains both types of these hair fibers.

We have found that we may permanently wave such a head of hair, where side-by-side hair fibers may be bleached and unbleached, if we wind the hair using a special "wrapping" aqueous composition and then applying a second special "processing" aqueous composition. The beneficial actions of the "wrapping" composition are best explained by the action of its ingredients.

Water is the vehicle which furnishes the aqueous carrying means for the other ingredients. Water alone plays a role in that the increased amount of water absorbed by the bleached fiber is directly related to the KSO₃H groups which have been formed during the bleaching. Thus with the application of the "processing" composition, there will be a dilution of its active ingredients within the bleached hair fiber, the greater the bleaching the more the dilution.

Most importantly, though, with this increased absorption of the aqueous vehicle, the water will carry the other ingredients to those parts of the bleached hair fibers which need their respective actions.

We have found that the more acidic sulfonic acid group of the bleached hair will exert a much higher absorptive reacting point than the natural occurring but weaker carboxylic group for certain substantive compounds containing a lipoidal alkyl chain having 10 or more carbon atoms. While fatty alcohols and fatty amines and fatty amides may be used, we have found particularly effective the compounds containing a quaternary ammonium group. Such compounds are well known in the trade and examples of these are listed in the CTFA Dictionary.

What has not been appreciated is the preferential absorption of such compounds by the KSO₃H groups in the bleached hair fiber, so that the most sensitive damaged parts of the bleached hair fibers are given a protection because of the hydrophobic action of the lipoidal side chain of such compounds. Thus, when the processing composition is subsequently applied, the bleached hair with such an absorbed hydrophobic side chain will repel the active components of the processing composition from these weakened points within the hair fiber.

A further advantage in the use of such substantive compounds with a lipoidal side chain is that they provide for easier handling and combing of the mixture of the bleached and unbleached hair fibers to form the small sections or tresses for wrapping on the waving rod.

Another ingredient that is carried by our aqueous wrapping composition to the interior of the hair is the disulfide of a mercaptan. While it is obvious that any water soluble disulfide may be used, we prefer to use the disulfide of the mercaptan used in the waving solution. The mercaptans most often used are the salts or glyceryl ester of thioglycolic acid. We thus use the first stage oxidation product of these mercaptans known as "di-thios," e.g., di-ammonium dithiodiglycolate or diglyceryl dithiodiglycolate. The higher absorption of the bleached hair will result in more of the "di-thio" compound in the wrapping lotion being carried into the bleached hair than in the unbleached hair.

The protective benefits of the "di-thio" compounds have been known. The permanent waving action is dependent upon a reaction in which the organic disulfide bonds of the hair are broken by reacting with a mercaptan. Since the reaction products are a hair mercaptan and the disulfide of the mercaptan, the reverse reaction is possible. Thus the smaller number of hair disulfide bonds of the bleached hair will have more additional disulfide bonds from the wrapping composition and thus further equalize the action of the mercaptan of the processing composition.

While the processing composition need only be the composition of presently marketed permanent waving lotions having a pH of about pH 7 to less than pH 9.5 and containing an alkaline salt of thioglycolate, preferably ammonium thioglycolate or an alkanolamine thioglycolate, with or without a carbonate, or the glyceryl ester of thioglycolate with a pH about pH 7, we have found it highly desirable with our processing composition to also include a substantial amount of the disulfide of the mercaptan.

The ratio of the mercaptan to the mercaptan disulfide is very important because sufficient hair disulfide bonds must be broken so "molecular flow" can take place to cause configuration change. Yet equilibrium must be reached before hair damage has occurred, particularly to the bleached hair fibers. The concentration by weight ratio must be maintained in the range one-to-ten to ten-to-one (1 to 10–10 to 1), and preferably the ratio should be in the very narrow range.

Since the speed of the reaction to the equilibrium point is dependent also on temperature, the processing composition must be warmed externally or it may be done by an exothermic reaction involving the oxidation of part of the mercaptan with an oxidizing agent, hydrogen peroxide or an iodate or a bromate. This can be done in such a way that part or all of the needed disulfide can be formed "in situ" just prior to applying the warm processing composition.

Our preferred processing composition contains glyceryl monothioglycolate and diglyceryldithioglycolate. This composition will reach an equilibrium state at a faster rate at about pH 7 than the thioglycolate salts. At about pH 7 and lower we thus obtain stronger salt bonding due to the greater number of salt linkages from the sulfonic acid groups found in the bleached hair.

When such a processing composition is used, we have found that it is desirable to adjust the pH of the wrapping composition to a pH in the range of pH 3 to pH 6 and preferably about pH 4. While any usually acidic pH adjusting material may be used, we prefer, when necessary, citric acid.

We have found that another useful ingredient in our system for waving a mixture of bleached and unbleached hair fibers is a poly-hydroxyl alkyl compound, such as propylene glycol, sorbitol, or glucose. However, glycerine is our preferred compound. This ingredient may be a component of the wrapping composition or of the processing composition or of both. Its concentration must be carefully controlled for too high a concentration in the final system will result in unsatisfactory waving of the unbleached hair fibers.

We have found that there is an optimum concentration range and a preferred concentration wherein the unbleached hair may be satisfactorily permanently waved, and the bleached hair is protected. It probably is due to a higher concentration ratio of glycerine to mercaptan being present in the bleached hair.

When used only in the wrapping composition we have found the concentration should not exceed 40%. When we have included it only in the waving composition we have found the concentration should not exceed 15%. It is thus apparent that lower concentrations must be used when it is included in both compositions; lower concentration in one composition requiring a higher concentration in the other.

Salts such as the sulphates, chlorides, bromides of sodium, potassium and ammonia have also been found to be useful. However, they should not be used in an amount greater than 5%, and are more effective when used in the processing compositions. Detergents, such as the salts of fatty alcohol sulphates are useful for wetting and emulsifying properties.

The invention accordingly comprises compositions of matter possessing the characteristics, properties, and the relation of constituents discussed above, which is exemplified in the compositions hereinafter detailed, with the scope of the invention being indicated in the claims.

BEST MODE FOR CARRYING OUT THE INVENTION

In order to clearly and precisely define the unique compositions we have developed for the wrapping lotion and the processing lotion, we have detailed in the following tables the general formulations and the preferred compositions for both the wrapping lotion and the processing lotion. By using these detailed formulations, one skilled in this art would be able to practice our unique discovery and would be able to achieve the permanent waving of a mixed bleached and unbleached head of hair, without requiring the segregation of the hair fibers into bundles of similarly conditioned hair fibers.

In Table I, the composition of the wrapping lotion we have developed is detailed, with the ranges for each ingredient indicated therein.

TABLE I

|  | % by Wgt/Volume |
| --- | --- |
| Mineral Oil | 0.1 to 1% |
| Fatty Alcohol, with between 10 and 18 carbon atoms | 0.1 to 1% |
| Polyoxyethylene either of Fatty Alcohols | 0.05 to 0.5% |
| Lauryl Sulphate Salt | 0.05 to 0.5% |
| Quaterniums (CTFA Dictionary) | 0.1 to 1.0% |
| Polyhydroxyl Compound | 0 to 40% |
| Dithiodiglycolate | 0 to 40% |
| Water | q.s. to 100% |

In Table II, the preferred embodiment of our wrapping composition is identified.

TABLE II

|  | % by Wgt/Volume |
| --- | --- |
| Mineral Oil - Viscosity | 0.2 to 0.5% |
| Lauryl Alcohol | 0.2 to 0.5% |
| Polyoxyethylene (20) ether of cetyl alcohol | 0.1 to 0.3% |
| Sodium Lauryl Sulfate | 0.1 to 0.3% |
| Oleyl Dimethyl Benzyl Ammonium Chloride | 0.2 to 0.5% |
| Glycerine | 0.0 to 15% |
| Diglyceryldithiodiglycolate | 1.0 to 15% |
| Water | q.s. to 100% |

In Table III, the formulation of our unique processing composition is identified, with the ranges for each constituent clearly detailed.

TABLE III

|  | % by Wgt/Volume |  |  |
| --- | --- | --- | --- |
| A Thioglycolate Ester or Salt | 10 | to | 305 |
| A Dithiodiglycolate Ester or Salt | 0 | to | 15% |
| Polyhydroxyl Compound | 0 | to | 15% |
| Salt | 0 | to | 3% |
| Water | q.s. | to | 100% |
| pH adjustments may be made with alkanolamines, ammonia or the carbonates of ammonia. | | | |

In Table IV, the preferred embodiment of our processing composition is defined.

TABLE IV

|  | % by Wgt/Volume |  |  |
| --- | --- | --- | --- |
| Glyceryl Monothioglycolate | 15 | to | 25% |
| Diglyceryldithiodiglycolate | 0 | to | 12% |
| Glycerine | 0 | to | 12% |

TABLE IV-continued

|  | % by Wgt/Volume |  |  |
| --- | --- | --- | --- |
| Sodium Bromide | 0 | to | 2% |
| Water | q.s. | to | 100% |
| pH adjusted with ammonia to | 6.5 | to | 7.5 |

Preferably, our hair waving system will be sold as an article of commerce, with the package containing two suitable plastic or glass containers. The wrapping composition should be in a container suitable for holding ¾ oz to 1¼ oz of the wrapping lotion, with 1 oz being preferred. For the processing composition, 3½ oz to 4 oz of the processing lotion should be contained, with 3¾ oz of the processing composition being preferred. Preferably a neutralizing composition should also be included in the package and, while it may be solution containing 10% of sodium bromate, we prefer a plastic or glass container with 2.3% of hydrogen peroxide.

The preferred method for using our article of commerce with our unique composition is as follows. After shampooing and towel drying the hair, thoroughly wet the hair with the wrapping composition. Section and wrap the hair on the selected, properly sized rods. Wet the hair thoroughly with the waving composition by applying twice to each wound curl, processing for not less than fifteen minutes. Rinse the hair thoroughly with tepid water. Pat with a towel to remove excess water and apply at least half of the neutralizing composition to the wound curls. Wait 5 minutes, then remove the rods and work the remaining neutralizing composition through the hair for one minute. Rinse with water, and the permanent waving of the hair is done.

It will thus be seen that the objects set forth above, among those made apparent from the preceding description, are efficiently attained and, since certain changes may be made in the above compositions without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

Having described our invention, what we claim as new and desire to secure by Letters Patent is:

1. A composite product for permanently waving a head of hair having hair fibers of vastly diverse condition intermixed throughout the head of hair, including up to 50% bleached hair fibers intermixed with unbleached hair fibers, and eliminating the necessity for segregation of the hair fibers into groups of hair fibers of similar condition, the composite product comprising A. a first, wrapping composition for readying the hair fibers by equalizing the diverse condition of the hair fibers, imparting protection to all of the hair fibers, and preparing the hair fibers for interactive receipt of the second composition, the first composition comprising an aqueous solution consisting essentially of, in addition to water:

(a) a disulfide derivative of a mercaptan incorporating at least one substituent group, and (b) a hair substantive organic compound incorporating a lipoidal alkyl chain and having a total of between about 10 and 18 carbon atoms; and B. a second, processing composition absorbable into the readied hair fibers for imparting a permanent wave thereto, comprising an aqueous solution consisting essentially of, in addition to water,
   (a) a thioglycolate ester or salt, and
   (b) at least one selected from the group consisting of mercaptans with at least one substituent group and disulfide derivatives of mercaptans with at least one substituent group, whereby a head of hair having mixed hair fibers of vastly differing conditions is capable of being permanently waved as a single entity, without requiring segregation of the hair fibers into groups of hair fibers of similar condition and without experiencing either breakage of the bleached hair fibers or under-waving of unbleached hair fibers, by readying all of the hair fibers for receipt of the waving composition and employing a waving composition formulated for optimum interaction with the readied hair fibers.

2. The permanent hair waving product defined in claim 1, wherein the first, wrapping composition further comprises an alkyl polyhydroxyl compound.

3. The permanent hair waving product defined in claim 1, wherein the first composition is further defined as being adjusted to have a pH below 7 and the second composition is adjusted to have a pH of about 7.

4. The composite product defined in claim 1, wherein the hair substantive organic compound comprises one selected from the group consisting of fatty alcohols, fatty amines, fatty amides, and compounds containing a quaternary ammonium group.

5. A composite product for permanently waving a head of hair having hair fibers of vastly diverse condition intermixed throughout the head of hair, including up to 50% bleached hair fibers intermixed with unbleached hair fibers, and eliminating the necessity for segregation of the hair fibers into groups of hair fibers of similar condition, the composite product comprising:

A. a first composition for readying the hair fibers by equalizing the diverse condition of the hair fibers, imparting protection to all of the hair fibers, and preparing the hair fibers for interactive receipt of the second composition, the first composition consisting essentially of
   (a) between about 0.1 and 1% by weight of a mineral oil,
   (b) between about 0.1 and 1% by weight of a fatty alcohol having between about 10 and 18 carbon atoms,
   (c) between about 0.05 and 0.5% by weight of a polyoxyethylene ether of fatty alcohols,
   (d) between about 0.05 and 0.5% by weight of a lauryl sulphate salt,
   (e) between about 0.1 and 1% by weight of a quaternium,
   (f) between about 0 and 40% by weight of a polyhydroxyl compound,
   (g) between about 0 and 40% by weight of a dithiodiglycolate, and
   (h) water forming the balance; and B. a second composition absorbable into the readied hair fibers for imparting a permanent wave thereto, comprising
   (a) between about 10 and 30% by weight of a thioglycolate ester or salt,
   (b) between about 0 and 15% by weight of a dithiodiglycolate ester or salt,
   (c) between about 0 and 15% by weight of a polyhydroxyl compound,
   (d) between about 0 and 3% by weight of a salt, and
   (e) water forming the balance, whereby a head of hair having mixed hair fibers of vastly diverse condition is able to be permanently waved as a single entity, without requiring segregation of the hair fiber into groups of hair fibers of similar conditions and without experiencing either breakage of the more damaged hair fibers or under-waving of the least damaged hair fibers, by readying the hair fibers for receipt of the waving composition and employing a waving composition formulated for optimum interaction with the readied hair fibers.

6. The permanent hair waving system defined in claim 5, wherein the pH of the second composition is adjusted by employing one selected from the group consisting of alkanolamines, ammonia, and carbonates of ammonia.

7. The permanent hair waving system defined in claim 6, wherein the pH of the second composition is adjusted to between about 6.5 and 9.5.

8. The permanent hair waving system defined in claim 5, wherein the pH of the first composition is adjusted to be between about 3 and 6 by employing an acidic pH adjusting material.

9. The permanent hair waving system defined in claim 5, wherein the polyhydroxyl compound comprises one selected from the group consisting of glycerine, propylene glycol, sorbitol, and glucose.

10. A wrapping composition for use on a head of hair having hair fibers of vastly diverse condition intermixed throughout the head of hair, including up to 50% bleached hair fibers intermixed with unbleached hair fibers, and eliminating the necessity for segregation into groups of hair fibers of similar condition, the wrapping composition being capable of equalizing the diverse condition of the hair fibers, imparting protection to all of the hair fibers, and preparing the hair fibers for interactive receipt of a waving solution, and consisting essentially of
   A. a water-soluble disulfide derivative of a mercaptan having at least one substituent group,
   B. an organic quaternary compound containing an alkyl chain of at least 10 carbon atoms, and
   C. water in sufficient quantity to form an aqueous carrier;

whereby heads of hair previously unable to be permanently waved without segregation of the hair fibers, are now able to be treated as a single entity by protecting, conditioning, equalizing, and preparing all of the hair fibers for receipt of a permanent waving solution, without experiencing breakage of the bleached hair fibers or under-waving of the unbleached hair fibers.

11. The wrapping composition defined in claim 10, wherein said composition further comprises an organic alkyl hydroxyl compound.

12. A wrapping composition for use in permanently waving a head of hair having up to 50% bleached hair fibers mixed with unbleached hair fibers, without requiring segregation into groups of hair fibers of similar condition, the wrapping composition being designed for thoroughly wetting the hair prior to wrapping about curling rods and consisting essentially of
   A. diglyceryldithiodiglycolate, B. a quaternary compound, and C. water in sufficient quantities to provide an aqueous carrier;

whereby said wrapping composition simultaneously performs as a hair equalizer, conditioner, and protector for subsequently receiving a waving composition without detrimental effect to the diverse hair fibers.

13. The wrapping composition defined in claim 12, wherein said composition further comprises glycerine.

14. The wrapping composition defined in claim 11, wherein said wrapping composition is further defined as having a pH adjusted to be below 7.

15. A composite product for permanently waving a head of hair having hair fibers of vastly diverse condition intermixed throughout the head of hair including up to 50% bleached hair fibers intermixed with unbleached hair fibers, and eliminating the necessity for segregation of the hair fibers into groups of hair fibers of similar condition, the composite product comprising A. a first composition for application to the hair prior to wrapping the hair about a curling rod in order to ready the hair fibers by equalizing the diverse condition of the hair fibers, imparting protection to all of the hair fibers, and preparing the hair fibers for interactive receipt of the second composition, the first composition consisting essentially of
  (a) between about 0.2 and 0.5% by weight of mineral oil,
  (b) between about 0.2 and 0.5% by weight of lauryl alcohol,
  (c) between about 0.1 and 0.3% by weight of polyoxyethylene ether of cetyl alcohol,
  (d) between about 0.1 and 0.3% by weight of sodium lauryl sulfate,
  (e) between about 0.2 and 0.5% by weight of oleyl dimethyl benzyl ammonium chloride,
  (f) between about 0 and 15% by weight of glycerine,
  (g) between about 1.0 and 15% by weight of diglyceryldithiodiglycolate, and
  (h) water forming the balance; and B. a second composition absorbable into the readied hair fibers and formulated for optimum waving interaction therewith, consisting essentially of
  (a) between about 15 and 25% by weight of glyceryl monothioglycolate,
  (b) between about 0 and 12% by weight of diglyceryldithiodiglycolate,
  (c) between about 0 and 12% by weight of glycerine,
  (d) between about 0 and 2% by weight of sodium bromide, and
  (e) water forming the balance, whereby the first composition provides a wrapping lotion which readies the hair fibers for receipt and interaction with the waving lotion, thereby assuring that the diversely conditioned hair fibers absorbed the required amount of waving lotion to produce a uniformly permanently waved head of hair regardless of the initial variations in the hair fiber's color and condition.

16. A method for permanently waving a head of hair haiving up to 50% bleached hair fibers mixed with unbleached hair fibers comprising the following steps:

A. wetting a section of the hair with a wetting and wrapping composition consisting essentially of
  (a) a disulfide of a mercaptan,
  (b) a quaternary ammonium compound with a lipoidal side chain of at least 10 carbon atoms, and
  (c) water in sufficient quantity to form an aqueous carrier;

B. wrapping the section of hair comprising both bleached and unbleached hair fibers on a rod of the desired diameter;

C. repeating the above steps until the entire head of hair has been treated with the wrapping composition and wrapped onto rods;

D. treating the wound hair on each rod with a waving and processing composition comprising
  (a) a mercaptan selected from the group consisting of ammonium, alkanolamine thioglycolate, glyceryl thioglycolate, and thioglycerol,
  (b) a dithio derivative of at least one of the mercaptans defined above, and
  (c) water in sufficient quantities to form an aqueous carrier;

E. rinsing the hair with water;

F. drying the rinsed hair with a towel;

G. treating the towel dried hair with an aqueous solution of an oxidizer selected from the group consisting of hydrogen peroxide, perborate bromates, and iodates; and H. rinsing the hair with water.

17. The method defined in claim 16, comprising the additional step of

I. adjusting the pH of the processing composition to be between about 7 and 9.5 by adding an alkaline agent to the composition, said alkaline agent being selected from the group consisting of ammonia, alkanolamines, and carbonic salts of ammonia and alkanolamines.

18. The method defined in claim 16, wherein the processing composition is further defined as comprising glyceryl thioglycolate as the mercaptan, diglyceryldithiodiglycolate as the dithio of the mercaptan, the pH is adjusted to be about 7, and hydrogen peroxide is employed as the neutralizer.

* * * * *